United States Patent [19]

Hosokawa

[11] Patent Number: 4,521,905
[45] Date of Patent: Jun. 4, 1985

[54] MONITOR OF AN X-RAY RADIATION RANGE

[75] Inventor: Yoshinori Hosokawa, Kyoto, Japan

[73] Assignee: Horiba, Ltd., Kyoto, Japan

[21] Appl. No.: 459,039

[22] Filed: Jan. 17, 1983

[30] Foreign Application Priority Data

Feb. 2, 1982 [JP] Japan .................................. 57-15900

[51] Int. Cl.³ .......................... G01N 23/20; G21K 1/00
[52] U.S. Cl. ......................................... 378/206; 378/50
[58] Field of Search ............................ 378/44, 50, 206

[56] References Cited

U.S. PATENT DOCUMENTS

| | | | |
|---|---|---|---|
| 1,976,179 | 10/1934 | Mannl | 378/206 |
| 3,628,021 | 12/1971 | MacDonald | 378/206 |
| 3,629,594 | 12/1971 | Sandberg | 378/206 |
| 4,060,733 | 11/1977 | Franke | 378/206 |
| 4,167,675 | 9/1979 | Stödberg et al. | 378/206 |
| 4,178,513 | 12/1979 | Dubois et al. | 378/44 |
| 4,406,015 | 9/1983 | Koga | 378/50 |

Primary Examiner—Bruce C. Anderson
Assistant Examiner—T. N. Grigsby
Attorney, Agent, or Firm—Wenderoth, Lind & Ponack

[57] ABSTRACT

X-rays and visible ray can be simultaneously incident upon the same range of an object to be radiated by making an axis of X-rays radiated be identical or almost identical with an axis of visible ray reflected.

X-rays can be accurately radiated on the point, on which visible ray was projected, without secular change even though the surface of said object to be radiated, on which X-rays are radiated, is rough.

1 Claim, 3 Drawing Figures

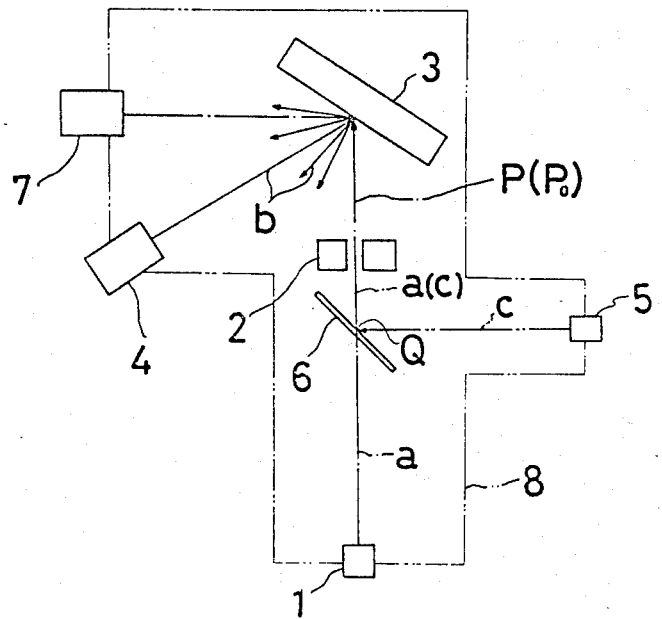

MONITOR OF AN X-RAY RADIATION RANGE

BACKGROUND OF THE INVENTION

1. Field of the Invention

The present invention relates to a monitor of an X-ray radiation range for an object to be radiated.

2. Description of the Prior Art

According to the conventional monitor of an X-ray radiation range, said X-ray radiation range for an object to be radiated can be visually confirmed, that is to say, as shown in for example FIG. 1, an X-ray (a) radiator (1) and a visible ray (c) projector (5) can be moved by the distance equivalent to a pitch (l) between an axis (P) of radiant X-ray and an axis ($P_1$) of visible ray so that X-rays may be radiated on the desired range of an object to be radiated. At first said visible ray (c) is projected on the desired range of said object (3) to be radiated and then said X-ray radiator (1) is moved so as to set said axis (P) of radiant X-ray to the position where said axis ($P_1$) of visible ray was placed. X-rays (a) are radiated on the desired range of said object (3) to be radiated by radiating X-rays (a) under this condition.

However, such a conventional monitor means has the following disadvantages:

The projection of visible ray (c) and the radiation of X-rays (a) can not be simultaneously carried out, thereby such a secular change that elements are oxidized during the time when said visible ray projector (5) and said X-ray radiator (1) are changed in positions is produced in the case when said elements contained in various kinds of metal and mineral are analyzed with them as said object (3) to be radiated. In addition, the above described changes of position must be repeatedly carried out at every time when said X-ray radiation range is changed, thereby such a conventional monitor means is remarkably inferior in maneuverability.

Furthermore, according to another conventional monitor means as shown in FIG. 2, an X-ray radiator (1) and a visible ray projector (5) are arranged so that an axis (P) of X-ray may intersect an axis ($P_1$) of visible ray so as to set the surface of an object (3) to be radiated, on which X-rays are incident, to a point of intersection of said axes (P), ($P_1$), thereby the radiation of X-rays (a) and the projection of visible ray (c) can be simultaneously carried out and the process of changing X-ray (a) radiation range can be improved. However, even this means has the following disadvantages:

Only an object having a flat surface, on which X-rays are incident, can be used for said object (3) to be radiated. That is to say, as shown in an enlarged scale in FIG. 2, the point, on which X-rays (a) are radiated, and the point, on which visible ray (c) is projected, have a location lag therebetween, when the surface of said object to be radiated, on which X-rays are radiated, is rough, thereby X-rays (a) are radiated on the range beside a visible ray projection range. As a result the radiation of X-rays (a) and the projection of visible ray (c) can be simultaneously carried out but the detecting range of X-rays (a) is different from that of visible ray (c).

The monitor means as shown in FIG. 2 also has such a disadvantage that the radiation range of X-rays (a) is different from that of visible ray (c) owing to a slight location lag between the surface, on which X-rays are radiated, and the point of intersection of X-rays (a) and visible ray (c).

SUMMARY OF THE INVENTION

The present invention was achieved in respect of the above described actual state. Thus it is an object of the present invention to provide a monitor of an X-ray radiation range, which can make the radiation range of X-rays identical with that of visible ray and can simultaneously carry out the radiation of X-rays and the projection of visible ray.

BRIEF DESCRIPTION OF THE DRAWINGS

FIG. 1 and FIG. 2 is a diagram showing the conventional monitor of an X-ray radiation range, respectively, and FIG. 3 is a diagram showing a monitor of an X-ray radiation range according to the present invention.

DETAILED DESCRIPTION OF THE PREFERRED EMBODIMENT

The preferred embodiment of the present invention will be described below by reference to the drawings.

Referring now to FIG. 3, (1) designates an X-ray radiator (for example X-ray tube) by which X-rays (a) are radiated on the sample such as various kinds of metal and mineral (one example of objects (3) to be radiated) through a collimator (2) for collecting X-rays (a) into a parallel pencil.

(4) designates an energy-dispersive type fluorescence X-ray detector for detecting fluorescence X-rays (b) radiated in correspondence to elements contained in said sample (3) when X-rays (a) are radiated on said sample (3) to simultaneously analyze the kind and the concentration of each element contained in said sample (3) on the basis of an energy level of said fluorescence X-rays (b).

Although a wave length-dispersive type fluorescence X-ray detector, which is used for said detector (4), also can carry out the qualitative analysis and the quantitative analysis, the use of an energy-dispersive type fluorescence X-ray detector makes the simultaneous analysis of a plurality of elements possible. In addition, the analysis can be carried out even though the signal of said fluoresence X-rays (b) is weak, thereby the composition of said sample (3) can be analyzed with a sufficient accuracy even though a diameter of said collimator (2), which changes the signal amount of X-rays (a) in proportion to a square of a diameter thereof, and as a result a radiation range of said X-rays (a) is become smaller. This is advantageous for the analysis of a plurality of elements in a minute range.

(5) designates a visible ray projector for projecting visible ray (c) such as visible laser ray, modulated light and monochromatic light, (6) designating an X-ray permeable mirror for transmitting said X-rays (a) and at the same time reflecting said visible ray (c), which has a mirror-finished surface as a visible ray-reflecting surface at least at one side thereof, said visible ray-reflecting surface being made of foil of metals having smaller atomic numbers such as aluminium and beryllium which have high transmission factor of said X-rays (a), and said visible ray-reflecting surface being arranged between said X-ray radiator (1) and said collimator (2) so that it may be inclined against an axis (P) of X-rays radiated in the lower reaches of said X-rays radiated.

The reflecting angle of said visible ray (c) is adjusted so that said visible ray (c) may be projected from said visible ray projector (5) on an X-ray transmitting position Q of said reflecting surface and at the same time an axis ($P_o$) of said visible ray (c) reflected may be identical or almost identical with said axis (P) of said X-rays radiated.

As described above, said axis (P) of X-rays radiated is arranged identically with said axis ($P_o$) of visible ray (c) reflected, thereby said X-rays (a) can be radiated on a visible ray projecting range of said sample (3), in short said visible ray projecting range is no other than an X-ray radiating range. That is to say, said X-rays (a) and said visible ray (c) are able to be incident upon simultaneously the same range of said sample (3).

(7) designates a detector for detecting visually said visible ray (c) projected on said sample (3), which comprises a microscope, a telescope and the like, said X-ray radiation range of said sample (3) being detected by detecting said visible ray projecting range of said sample (3).

Said X-rays (a) can be radiated on the desired range by a remote control of the position of said sample (3) by means of said detector (7) as a monitor, thereby fluorescence X-rays radiated from the desired range can be continuously detected.

(8) designates a case surrounding an X-ray radiating space which is preferably made of iron in respect of mechanical strength and cost and has a thickness of about 20 mm. Said case (8) may be made of lead and have a thickness of about 2 mm.

Furthermore, although the sample such as metal and mineral is used as said sample (3) to be radiated in the preferred embodiment, other gaseous, liquidous and slurry samples may be used also.

It is necessary only to flow or close up gaseous and liquidous samples in a cell made of polyester, beryllium and the like in the case of using gaseous and liquidous samples while it is necessary only to radiate said X-rays (a) downwardly and place slurry samples on an axis of said X-rays (a) radiated in case of using slurry samples.

A monitor of an X-ray radiation range according to the present invention also can be applied in an X-ray diffractometer, an X-ray absorption analyzer, medical X-ray radiating apparatus and the like in addition to the above described fluorescence X-ray analyzer.

As described above, according to the present invention, an axis of X-rays radiated on an object to be radiated is identical or almost identical with an axis of visible ray reflected, thereby X-rays and visible ray can be simultaneously incident upon the same range of an object to be radiated, as a result X-rays can be accurately radiated on the point, on which visible ray was projected, without secular change even though the surface of said object to be radiated, on which X-rays are radiated, is rough. Furthermore, an X-ray radiation range can be very easily changed. This is an advantage in the continuous detection. Thus a monitor of an X-ray radiation range, which is useful in spite of a remarkably simple improvement, can be provided.

What is claimed is:

1. A monitor of an X-ray radiation range for use in a fluorescent X-ray analyzer, said monitor comprising:
    an X-ray source for radiating X-rays on a sample to be irradiated;
    a collimator arranged along an axis of said X-rays so as to collimate said X-rays;
    a mirror which is permeable to said X-rays but which reflects visible rays, said mirror being arranged across said axis of said X-rays between said collimator and said X-ray source;
    a visible ray source arranged so as to radiate visible rays which are reflected by said mirror and then pass through said collimator so as to irradiate said sample, said visible rays being irradiated simultaneously with said X-rays;
    a fluorescence detector for detecting fluorescence X-rays emitted from said sample in response to said X-rays radiated thereon by said X-ray source;
    an optical viewer arranged so as to view a point on said sample upon which said X-rays impinge;
    wherein said mirror is inclined at an angle with respect to said X-ray axis so that an axis of said visible rays is substantially identical to said axis of said X-rays radiated by said X-rays source, whereby said point on said sample upon which said X-rays impinge is substantially identical to a point on said sample upon which said visible rays impinge and said point is simultaneously irradiated with both said X-rays from said X-ray source and said visible rays from said visible ray source.

* * * * *